United States Patent [19]

Macher

[11] Patent Number: 5,284,967
[45] Date of Patent: Feb. 8, 1994

[54] PLEUROMUTILINS

[75] Inventor: Ingolf Macher, Wörgl, Austria

[73] Assignee: Biochemie Gesellschaft m.b.H., Tyrol, Austria

[21] Appl. No.: 946,267

[22] Filed: Sep. 16, 1992

Related U.S. Application Data

[62] Division of Ser. No. 591,913, Oct. 2, 1990, Pat. No. 5,164,526.

[30] Foreign Application Priority Data

Oct. 3, 1989 [AT] Austria ................................ 2286/89
Oct. 3, 1989 [AT] Austria ................................ 2287/89

[51] Int. Cl.$^5$ ............................................. C07C 323/23
[52] U.S. Cl. ..................................................... 560/153
[58] Field of Search ................ 560/153, 16, 118, 121, 560/123, 138, 205, 220, 179, 183, 188, 194

[56] References Cited

U.S. PATENT DOCUMENTS

| | | | |
|---|---|---|---|
| 3,919,290 | 11/1975 | Egger et al. ........................ | 560/153 |
| 4,086,359 | 4/1978 | Dursch ................................ | 560/153 |
| 4,107,434 | 8/1978 | Waldvogel ........................ | 560/153 |
| 4,390,558 | 6/1983 | Ridgeway et al. ............. | 514/550 X |
| 4,584,407 | 4/1986 | Hollowood ........................ | 564/487 |
| 4,675,330 | 6/1987 | Berner et al. .................... | 560/153 |
| 5,017,725 | 5/1991 | Hohmann et al. .............. | 564/487 |

Primary Examiner—Arthur C. Prescott
Attorney, Agent, or Firm—Robert S. Honor; Melvyn M. Kassenoff; Thomas O. McGovern

[57] ABSTRACT

Compounds of formula I

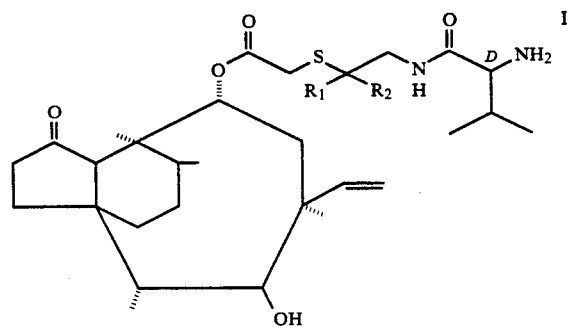

wherein $R_1$ and $R_2$ are the same or different and each represent hydrogen, alkyl, alkenyl, cycloalkyl, aryl or aralkyl are produced by a new environmentally acceptable process.

3 Claims, No Drawings

PLEUROMUTILINS

This is a division of application Ser. No. 07/591,913, filed Oct. 2, 1990, now U.S. Pat. No. 5,164,526.

This invention relates to a novel process for the preparation of a compound of formula

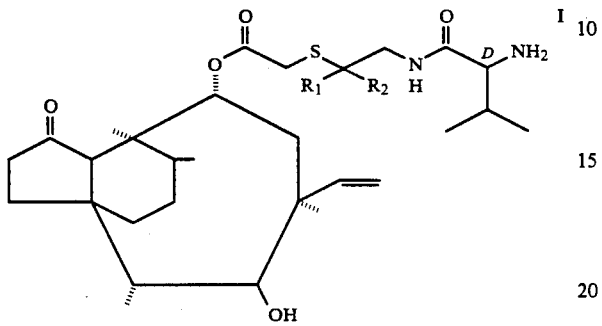

wherein $R_1$ and $R_2$ are the same or different and each represent hydrogen, alkyl, alkenyl, cycloalkyl, aryl or aralkyl, and intermediates for use in this process.

These compounds are mutilin derivatives which are known from U.S. Pat. No. 4,675,330 as useful veterinary agents in particular for the chemotherapeutic treatment of pigs.

The compounds may be used in e.g. free base form or acid addition salt form, preferably acid addition salt form.

In formula I alkyl may be straight or branched chain. Preferably alkyl means lower alkyl, e.g. 1 to 4 carbon atoms. Alkenyl has preferably 2 to 4 carbon atoms and is especially allyl. Aryl is preferably phenyl. Aralkyl is preferably benzyl. Cycloalkyl has preferably 5 or 6 ring-members.

In one aspect the invention provides a process of the preparation of a compound of formula I as defined above, which comprises the step of (i) deprotecting a compound of formula II

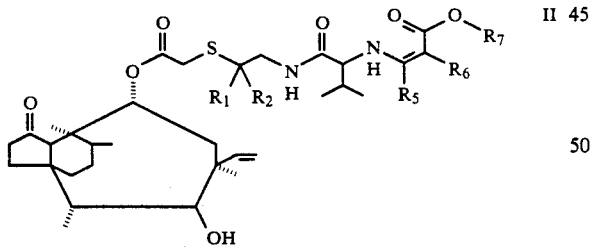

wherein
$R_1$ and $R_2$ are as defined above, and wherein
$R_5$ is alkyl,
$R_6$ is hydrogen or alkyl, and
$R_7$ is alkyl.

The reaction may be effected in conventional manner for the hydrolysis of an enamine group. For example the reaction may be effected under acidic conditions, e.g. with hydrochloric acid. The reaction may be effected e.g. at from about 10° to about 50° C., preferably at 20° C.

The compounds of formula II are new per se and also form part of the invention.

A compound of formula II is conveniently obtained by the step of (ii) appropriately acylating a compound of formula III

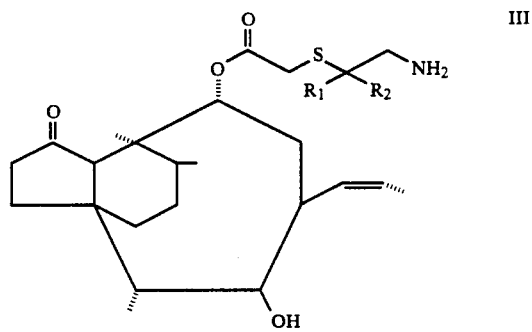

wherein $R_1$ and $R_2$ are as defined above. The acylation may be effected in conventional manner. Conveniently the acylation is effected with D-valine protected as an enamine, e.g. in the form of a Dane salt. These may be produced by reacting D-valine with a $\beta$-keto ester of formula $R_5$—CO—CH($R_6$)—COOR$_7$, wherein $R_5$, $R_6$ and $R_7$ are defined above, e.g. acetoacetic acid methyl ester. Preferably the D-valine is activated in the form of a carbonic acid anhydride, e.g. produced from chloroformic acid in situ. The acylation reaction is conveniently effected e.g. at from −20° C. to 0° C. The acylation solvent is for example tert.-butyl methyl ether.

A compound of formula III is conveniently obtained by the step of (iii) reacting a tosylate (Tos) of formula IV

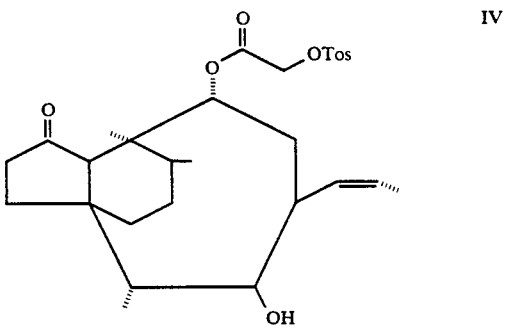

with a compound of formula V

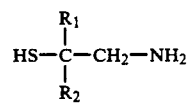

The reaction may be effected in conventional manner. Conveniently the reaction is effected in an organic solvent e.g. tert.-butyl methyl ether. Conveniently it is effected under alkaline conditions, e.g. sodium hydroxide solution. Preferably a phase transfer catalyst is present, e.g. benzyltributyl ammonium chloride.

The compound of formula IV may be produced e.g. by the step of (iv) tosylating a pleuromutilin of formula

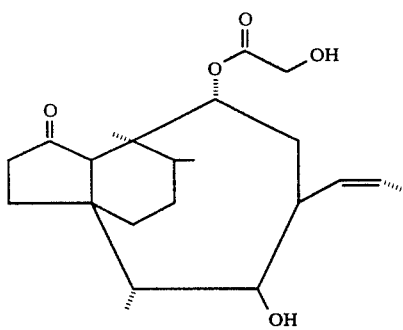

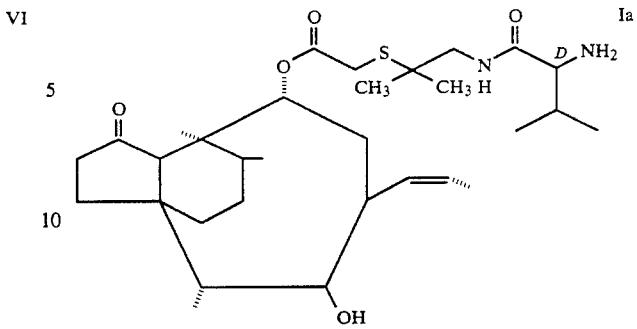

The reaction may be effected in conventional manner. The reaction steps of i) and ii) are preferably effected in a one-pot process, i.e. in the same reaction vessel e.g. without isolating the intermediates. The reaction steps iii) and iv) are preferably effected in a one-pot process.

The process according to the invention has great advantages in comparison with known processes, in particular the process is easy to handle on a technical scale and is environmentally acceptable.

In step iii) and iv) a pleuromutilin-cysteamine derivative may be obtained from pleuromutilin in a one-pot process. The reaction of the tosylate of formula IV to produce the cysteamine derivative has been effected up to now with sodium in ethanol. This may require long reaction times (about 15 hours), the work-up of the reaction mixture may require repeated extractions and the purification is effected by chromatography. In the present process the reaction may be effected employing sodium hydroxide and phase transfer catalysis in relatively short time (about 2 hours). The isolation of the pure crystalline product can be effected from the reaction mixture by filtration. No extraction and no chromatography is necessary. Small amounts of solvents and no chlorinated hydrocarbons are employed, and so the process is environmentally acceptable.

For the acylation of a compound of formula III a protected, activated D-valine is employed. Until now conventional protecting groups, e.g. t-butoxycarbonyl, benzyloxycarbonyl or trichloroethoxycarbonyl for the protection of the amino function have been employed. The corresponding esters used for the protection are expensive and sometimes also toxic and/or caustic. In comparison in the present process the protection of the amino function is effected by reaction of D-valine with a β-keto ester e.g. to form a D-valine Dane salt. Up to now the activation has been effected with dicyclohexylcarbodiimide and nitrophenol to form an active ester. In the present process a mixed anhydride is formed. This has the advantage that no waste material (dicyclohexylurea) is formed and the reaction may be simplified (no filtration, no evaporation, no isolation). The acylation of the pleuromutilincysteamine derivative of formula III employing a carbonic acid mixed anhydride method yields as side products only $CO_2$ and ethanol, not the difficult to handle 4-nitrophenol.

The removal of the protecting group may be effected e.g. by hydrolysis e.g. with hydrochloric acid and is significantly easier than the removal of previously used protecting groups.

A preferred embodiment of the invention relates to the preparation of the compound of formula Ia, the compound of formula Va

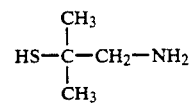

being used as starting material.

The present process for the production of compounds of formula I has the following advantages:

The process is easy to handle on a technical scale. It offers economical and ecological advantages such as cheap starting materials and as solvents for the steps i) to iv) only water and tert. butyl methyl ether, which can be easily recyclised.

By using tert. butyl methyl ether as a solvent the isolation of pleuromutilin-cysteamine is simplified.

The reaction steps iii) and iv) can be effected in a one-pot process. Also the formation of the hydrochloride can be effected by simply extracting with aqueous hydrochloric acid. Further advantages are no chromatography; no halogenated hydrocarbons; no waste material which requires costly disposal and no technologically difficult processes (e.g. such as hydrogenation).

The present invention also provides a process for the preparation of a compound of formula V which comprises cleaving a compound of formula

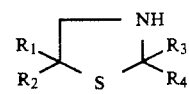

wherein $R_1$ and $R_2$ are as defined above and $R_3$ and $R_4$ are the same or different and are hydrogen, alkyl, alkenyl, cycloalkyl, aryl or aralkyl and preferably have the same meanings as $R_1$ and $R_2$. $R_3$ is preferably hydrogen. $R_4$ is preferably a branched chain lower alkyl, especially isopropyl.

The cleavage of a compound of formula VII may be effected in analogous manner to known methods. For example in an aqueous solution using a carbonyl reagent, e.g. that would react with the carbonyl group of aldehydes or ketones e.g. to form a hydrazone e.g. phenylhydrazine. The compounds may be isolated or used further in the form of an acid addition salt.

If desired the compounds of formula VII are not isolated but employed for further reaction in the aqueous solution in which they are obtained.

The ring cleavage may also be effected without employing a carbonyl reagent by e.g. steam-distillation, but the reaction time is longer.

The compounds of formula VII may be obtained by e.g. reducing a compound of formula VIII

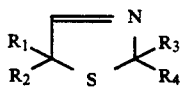

wherein $R_1$, $R_2$, $R_3$ and $R_4$ are as defined above.

The reduction of the compounds of formula VIII to the compounds of formula VII may be effected e.g. according to known reduction methods. For example, a thiazoline of formula VIII is suspended in water and reduced in an acidic medium by addition of $NaBH_4$, preferably in an aqueous solution. The compounds of formula VII may be isolated from the reaction mixture according to known processes and optionally purified.

The preferred compound of formula VII is the compound of formula VIIa

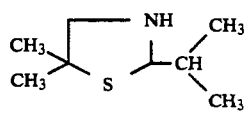

The compound of formula VIIa is new and forms part of the present invention. The compound may be obtained by reducing the compound of formula VIIIa The compound may be obtained by reducing the compound of formula VIIIa

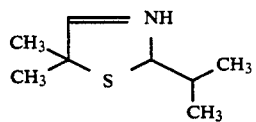

The process for the preparation of compounds of formula V of the present invention has the following advantages:

The process may comprise only 2 reaction steps, starting from compounds of formula VIII which are easily preparable in a technical scale. The intermediate of formula VII need not to be isolated or purified for the next reaction step. Simple reaction conditions may be employed, neither high temperatures nor high pressures. Cheap starting materials, water as reaction medium and high yields as well as a simple isolation by evaporating and crystallisation are some of the economic advantages of the process. No damage is inflicted on the environment owing to the lack of malodorous reagents or formation of side products.

The compounds of formula V represent a known class of intermediates for the production of valuable antibiotics. For their preparation the following processes are e.g. known:

1. α-aminothiole hydrochlorides may be prepared in laboratory scale by condensation of nitromethane, aldehyde or ketone and benzylmercaptane to give secondary mercaptoalkylamines, reduction of the nitro group with $LiAlH_4$ and reductive removal of the benzyl group with sodium in liquid ammonia. The process has following disadvantages: safety problems in handling large amounts of nitromethane (danger of explosion by reaction with bases, e.g. sec. amines), ecological problems stemming from the intensive, disagreeable smell of benzyl mercaptan, safety problems in handling larger amounts of $LiAlH_4$ in ether and in handling metallic sodium in liquid ammonia.

2. α-aminothioles may also be obtained by addition of ammonia or amines to episulfides. The cleavage of the thiirane ring is effected either at high temperatures (100°–200° C.) in a bomb tube or at lower temperatures (up to 60° C.) but employing silver salts in up to overstoichiometric amounts. The α-aminomercaptan is obtained from the silver complex by addition of hydrogen sulfide. The disadvantages of the process are: the episulfides have first to be obtained form the corresponding epoxides, the addition of amines to episulfides at higher temperature leads to bismercaptoethylated products and polymers, which are very difficult to separate. The use of silver salts for the cleavage of episulfide increases the costs and renders the precipitation of silver sulfide with the toxic and malodorous hydrogen sulfide necessary.

3. Reaction of disulfur dichloride with isobutyraldehyde yields the corresponding dialdehyde disulfide. The latter is reacted with a nitrogen compound to form an imine, which is reduced with $LiAlH_4$. The drawbacks of the process are: The dialdehyde disulfide is obtained after a long reaction time (2 days) and a two-fold vacuum distillation only in 40% yield and the reduction of the imine is difficult to be carried out on a larger scale due to safety problems owing to the use of ether and $LiAlH_4$. Free base forms of any of the compounds may be converted into acid addition salt forms and vice versa.

The following examples illustrate the invention whereby all temperatures are given in ° C.

EXAMPLE 1

2-Isopropyl-5,5-dimethylthiazolidine (formula VIIa)

78.6 g 2-isopropyl-5,5-dimethylthiazoline (formula VIIIa) are suspended in 80 ml distilled water in a 1 l four-necked flask with stirrer, thermometer, pH-electrode and 2 dropping funnels. The pH of the suspension is adjusted to pH 2 with 2N HCl (about 20 ml). The suspension is vigorously stirred and cooled with ice and treated simultaneously dropwise with hydrochloric acid (first 80 ml 2N HCl, then about 80 ml 6N HCl) and $NaBH_4$-solution (10 g in 100 ml $H_2O$) in such a manner that the inner temperature does not exceed 20° and the pH-value remains at 2. After the reaction is completed (TLC-control) the reaction mixture is extracted twice with tert. butyl methyl ether (1×250 ml, 1×50 ml). The ether phases are discarded. The colourless aqueous solution is treated with 250 ml tert. butyl methyl ether and the pH adjusted to 5.8 with 10N NaOH. The phases are separated. The aqueous phase is extracted with 50 ml tert. butyl methyl ether (whereby the pH value should not drop below 5.5). The etheral extracts are combined, stirred with 300 ml distilled water and the pH value adjusted to 2 with about 60 ml 6N HCl under cooling. The etheral phase is separated and discarded. The aqueous solution of 2-isopropyl-5,5-dimethylthiazolidine hydrochloride is used directly in the next step. The title compound can also be isolated by evaporation of the etheral phase of the second extraction and distillation in vacuo; whereby a colorless liquid, b.p. 76°–78° (14 mbar) is obtained.

$^1$H-NMR(CDCl$_3$): 1.00(d,3H,J=7 Hz,CH$_3$—CH):1.05(d,3H,J=7 Hz,CH$_3$—CH); 1.35 (s,3H,CH$_3$—C—S);1.45(s,3H,CH$_3$—C—S);2.20(m,1H,-CH—CH—(CH$_3$)$_2$); 2.30(s,1H,NH);2.75 and 3.00 (AB,2H, J$_{AB}$=15 Hz, H-4, H-4'); 4.50 (d,1H, J=7 Hz, H-2).

The reduction and the work-up are monitored by TLC. A part of the reaction mixture is treated with 10 parts methanol and 1 part 2N sodium hydroxide solution, brought directly to a plate, and ethylacetate is used as eluent. The detection is effected with UV light or spraying with molybdatophosphoric acid and heating to 150°.

| I | Rkg | Et-1 | W-1 | Et-2 | W-2 | II |
|---|---|---|---|---|---|---|
|   | O | O |   |   |   |   |
| O | O |   |   |   |   |   |
|   |   | O |   | O | O | O |
| x | x | x | x | x | x | x |

Rkg = Reaction mixture
Et-1 = Etheral phase of 1st extraction
W-1 = Aqueous phase of 1st extraction (pH 2)
Et-2 = Etheral phase of 2nd extraction
W-2 = Aqueous phase of 2nd extraction (pH 5.8)

EXAMPLE 2

Dimethylcysteamine.Hydrochloride (compound of formula Va)

The aqueous phase obtained in Example 1 in a 1 l four-necked flask equipped with thermometer, pH-electrode and reflux condenser is covered with a layer of 300 ml toluene and treated under inert gas atmosphere with 50 ml phenylhydrazine. The mixture is vigorously stirred under inert gas atmosphere under reflux for 1½ to 2 hours until no starting material is detected (TLC control). The mixture is cooled to 20°-25°, treated with 20 ml acetone and stirred for 10 minutes. The phases are separated and the aqueous phase extracted 4 times with 50 ml toluene each time. Water is distilled off at 90° under a weak vacuum.

The solid residue is dried well in the reaction vessel (60° bath temperature) and then dissolved in 100 ml hot absolute ethanol. The solution is cooled to room temperature under stirring and treated slowly dropwise with 300 ml tert.butyl methyl ether. The mixture is left overnight in a refrigerator to crystallize. The colorless crystals are filtered off, washed with a mixture of 20 ml ethanol and 100 ml tert.butyl methyl ether and dried at 50° in a vacuum shelf dryer to give 49.2 g (70%) of the title compound, m.p. 238° (subl.).

$^1$H-NMR(D$_2$O): 1.45 (s, 6H, 2xCH$_3$); 3.15 (s, 2H, CH$_2$-N).

The ring cleavage and the work up are followed by TLC. The toluene phases are brought directly to the TLC-plates, the aqueous phase first being diluted with methanol (1:10) and made alkaline with 1 part of 2N sodium hydroxide solution. Eluent: CH$_2$Cl$_2$/CH$_3$OH/NH$_4$OH=90/10/1.

Detection: spraying with molybdatophosphoric acid and heating to 150°.

| II | Phh | RkT | RkW | W | III |
|---|---|---|---|---|---|
| O | O | O | O | O |   |
|   |   |   |   | O |   |
|   |   |   | ∧ | ∧ | ∩ |
| x | x | x | x | x | x |

Phh = Phenylhydrazine
RkT = Reaction toluene phase
RkW = Reaction aqueous phase
W = Aqueous phase before evaporation

EXAMPLE 3

14-O-[1-((D)-2-Amino-3-methylbutyrylamino)-2-methyl propan-2-yl-thioacetyl]mutilin.Hydrochloride a) N-[3-Methoxy-1-methyl-3-oxo-1-propenyl]-D-valine.potassium salt (D-Valine Dane salt).

36.6 g solid KOH are dissolved in 1250 ml isopropanol under slight warming. 65 g D-valine are added, followed by 65.9 ml methyl acetoacetate. The mixture is stirred to give after about 10 minutes a light yellow solution, which is refluxed for 2 hours. The reflux condenser is replaced by a Claisen condenser and a short column (about 10 cm) and the water formed during the condensation reaction (2 Mol equivalents) removed by distilling off about 1100 ml isopropanol. Thereafter 500 ml isopropanol are added and again 500 ml isopropanol are distilled off. The still warm solution (which in the cold solidifies) is either poured on 3 l t.butyl methyl ether or diluted with the same amount of t.butyl methyl ether and stirred under ice-cooling for about 3 hours. The resulting suspension is left overnight at 4° under exclusion of moisture (the product is hygroscopic), filtered, washed with 500 ml tert.butyl methyl ether and dried at 40° to 50° overnight in a vacuum shelf dryer to give the heading compound, m.p. 212°-218°.

b) 14-O-[(1-Amino-2-methylpropan-2-yl)thioacetyl]-mutilin (formula III)

75.7 g Pleuromutilin, 42 g p-toluenesulfonyl chloride in 200 ml tert.butyl methyl ether, and 40 ml water are treated slowly in a 0.5 l Schmizo-reactor with stirrer, inner thermometer and reflux condensor with 50 ml 10N sodium hydroxide solution. The reaction mixture warms up to about 30°. The mixture is vigorously stirred and refluxed for 1 hour, thereafter the reaction being finished to give a tosylate of formula IV. The mixture is cooled to 25° and treated whilst stirring with 31.2 g dimethylcysteamine-hydrochloride, 3.2 g benzyltributyl ammonium chloride and 50 ml 10N sodium hydroxide solution. The inner temperature raises to 30°. The reaction mixture is vigorously stirred and heated to 40°-45°. After about 1 hour the reaction is complete. The mixture is diluted with 500 ml water, cooled to 0° and stirred at 0° for 15 minutes. Thereafter the mixture is filtered. The product is washed with water and cold tert.butyl methyl ether (twice with each 100 ml) and dried overnight in a vacuum dryer at 55°, to give the heading compound, m.p. 153°-155°.

If desired the second addition of 50 ml 10N sodium hydroxide may be omitted and instead 100 ml of 10N sodium hydroxide is added instead of the first addition of 50 ml 10N sodium hydroxide (to the pleuromutilin).

c) 14-O-[1-((D)-2-Amino-3-methylbutyrylamino)-2-methylpropan-2-yl-thioacetyl]mutilin-Hydrochloride 14 g D-Valine-Dane-salt are suspended in 200 ml tert.butyl methyl ether in a 0,5 l Schmizo-double jacketed reactor equipped with thermometer and stirrer. 6.6 ml N-methylmorpholin are added and the suspension cooled to −10°. To the cooled and stirred suspension are added within 5 minutes 5 ml chloroformic acid ethylester. The mixture is stirred 30 minutes at −10°. 23.3 g solid 14-O-[(1-amino-2-methylpropan-2-yl)thioacetyl]mutilin are added followed by 50 ml tert.butyl methyl ether. The mixture is stirred either for 60 minutes at 0° and 30 minutes at 20° or for 30 minutes at −10° and 60 minutes at 0°. The mixture is then extracted with 150 ml water.

Solution of a compound of formula II in tert.-butyl methyl ether results. The organic phase is treated with 200 ml water and the pH adjusted to 1.0-1.2 with about 14 ml 6N hydrochloric acid under vigorous stirring. The mixture is vigorously stirred at room temperature for 1 to 2 hours, and the pH value is kept constant by addition of 2N hydrochloric acid. The completion of the hydrolysis of the enamine protecting group is followed by HPLC. The organic phase is separated and the aqueous phase extracted 3 times with tert.butyl methyl ether 125 ml each in order to remove the acetoacetic acid ester. To the stirred aqueous phase are added 150 ml tert.butyl methyl ether and the pH adjusted to about 7 with 10N sodium hydroxide solution and then to pH 8.0-9.0 with 2N sodium hydroxide solution. The phases are separated, and the organic phase is extracted twice with water, 100 ml each. The etheral phase is treated with 150 ml water and the pH adjusted to 2.5-3.0 with 2N hydrochloric acid under vigorous stirring. The mixture is stirred for 5 minutes and the phases are separated. The tert.butyl methyl ether is removed in a rotavapor in vacuo at 30°. The heading compound is obtained by spray- or freeze drying from the aqueous solution.

I claim:

1. A compound of formula II

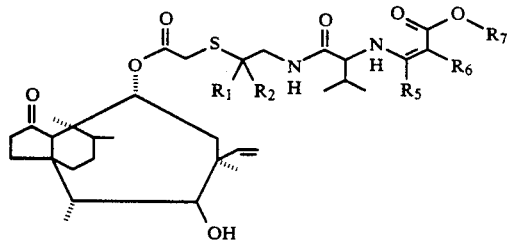

where

R₁ and R₂ are the same or different and each represent hydrogen, alkyl, alkenyl, cycloalkyl, aryl, or aralkyl;

R₅ is alkyl;

R₆ is hydrogen or alkyl;

R₇ is alkyl.

2. A compound of formula II

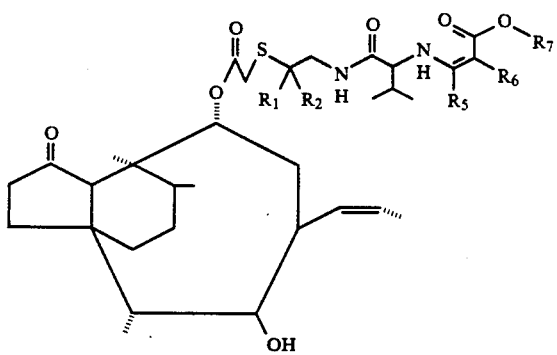

where

R₁ and R₂ are the same or different and each represent hydrogen, alkyl having 1 to 4 carbon atoms, alkenyl having 2 to 4 carbon atoms, cycloalkyl having 5 or 6 carbon atoms, phenyl, or benzyl;

R₅ is alkyl having 1 to 4 carbon atoms;

R₆ is hydrogen or alkyl having 1 to 4 carbon atoms; and

R₇ is alkyl having 1 to 4 carbon atoms.

3. The compound according to claim 1 of formula II

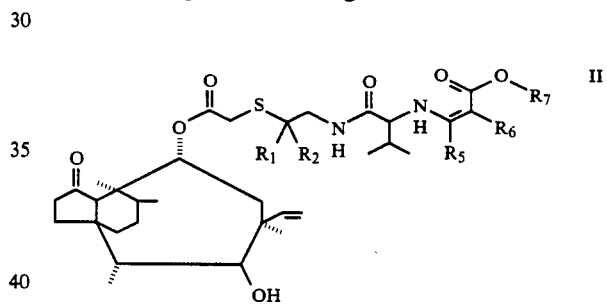

where

R₁ and R₂ are both methyl;

R₅ is methyl;

R₆ is hydrogen; and

R₇ is methyl.

* * * * *